United States Patent [19]

Erlanger et al.

[11] Patent Number: 5,405,785
[45] Date of Patent: Apr. 11, 1995

[54] DERIVATIVES OF CYCLOSPORINE A, ANTIBODIES DIRECTED THERETO AND USES THEREOF

[75] Inventors: Bernard F. Erlanger, Whitestone; William L. Cleveland, New York; Nicholas A. Cacalano, Irvington, all of N.Y.

[73] Assignee: The Trustees of Columbia University in the City of New York, New York, N.Y.

[21] Appl. No.: 6,169

[22] Filed: Jan. 15, 1993

Related U.S. Application Data

[63] Continuation of Ser. No. 869,219, Apr. 13, 1992, which is a continuation of Ser. No. 280,009, Dec. 5, 1988.

[51] Int. Cl.6 .......................................... G01N 33/545
[52] U.S. Cl. .................................. 436/531; 436/518; 436/528; 436/548; 435/7.92; 435/7.93; 435/7.94; 435/7.95; 530/371; 530/388.9
[58] Field of Search ......................... 435/7.1, 7.9–7.95, 435/7.92–7.95; 436/518, 528, 531, 548; 530/371, 387

[56] References Cited

PUBLICATIONS

Quesniaur, et al. (I), Potential of Monoclonal Antibodies Improve Therapeutic Monitoring of Cyclosporine, Clin Chem. 33/1, 1987 pp. 32–37.

Schran et al., Determination of Cyclosporine Concentrations with Monoclonal Antibodies, Clin Chem 33/12, 1987 pp. 2225–2229.

Quesniaux et al. (II), Time Specification & Cross-Reactivity of Monoclonal Antibodiese to Cyclosporine vol. 24, #11 pp. 1159–1168 1987.

Quesnioux et al. (I): "Potential of MAb . . . Cyclosporine" Clin Chem 33/1, 1987 pp. 32–37.

Schran et al. "Determination . . . with MAb" Clin Chem 33/12, 1987 pp. 2225–2229.

*Primary Examiner*—Christine M. Nucker
*Assistant Examiner*—Jeffrey Stucker
*Attorney, Agent, or Firm*—John P. White

[57] ABSTRACT

This invention provides a molecule comprising cyclosporine A or a congener of cyclosporine A which is photochemically attached to a ligand containing a reactive group. This invention also provides a composition of matter which comprises a conjugate of a compound and the aforementioned molecule wherein the compound is bound to the molecule through the reactive group. This invention further provides an antibody directed to the aforementioned composition of matter specific for cyclosporine A or congener of cyclosporine A. Finally, this invention provides a method of monitoring levels of cyclosporine A or congener of cyclosporine A in a subject.

35 Claims, 4 Drawing Sheets

RH = CsA (H = Hydrogen of CsA side chain)

DERIVATIVES OF CYCLOSPORINE A, ANTIBODIES DIRECTED THERETO AND USES THEREOF

This invention was made with government support under Grant Numbers RO1 NS-15581 and PO1 HL-36581 and training grants 2-T32-AI-07161-11 and T32-CA-09503 from the National Institute of Health, U.S. Department of Health and Human Resources. Accordingly, the U.S. Government has certain rights in the invention.

This is a continuation of application Ser. No. 07/869,219, filed Apr. 13, 1992, which is a continuation, of application Ser. No. 280,009, filed Dec. 5, 1988.

BACKGROUND OF THE INVENTION

Throughout this application, various publications are referenced by arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed in this application.

Cyclosporine A (CsA) is a cyclic undecapeptide of fungal origin which is an immunosuppressive agent useful in preventing organ rejection in transplant patients (1-3).

Because the therapeutic index of CsA is narrow, it is important to measure serum cyclosporine levels in patients treated with CsA (4). This can be accomplished by high performance liquid chromatography or by RIA, with the latter procedure being the more convenient one.

It has been reported, and we have confirmed (unpublished), that CsA, itself, is non-immunogenic (5). To obtain antibodies, therefore, it is necessary to link CsA to a protein carrier. The side chains of CsA, however, consist only of aliphatic groups with none of the functional groups customarily used to link a hapten to a carrier. Previous workers have made immunogenic cyclosporine C (CsC)-protein conjugates because CsC has a threonine residue in position 2 (5). Linkage to a protein was via a hemisucciniate, using a water soluble carbodiimide as a coupling agent. Polyclonal antisera were successfully raised in this way and are routinely used to measure CsA in patients sera (5). More recently, monoclonal antibodies were prepared using an activated ester of a lysyl-CsA derivative (6).

We have chosen to use CsA, itself, as a hapten by converting it to a reactive carboxyl-containing peptide via a photochemical reaction. Coupling of this derivative to proteins has led to the successful raising of CsA-specific rabbit antibodies that can be used to measure CsA levels in sera of transplant patients under treatment with CsA.

SUMMARY OF THE INVENTION

The present invention provides a molecule having the structure:

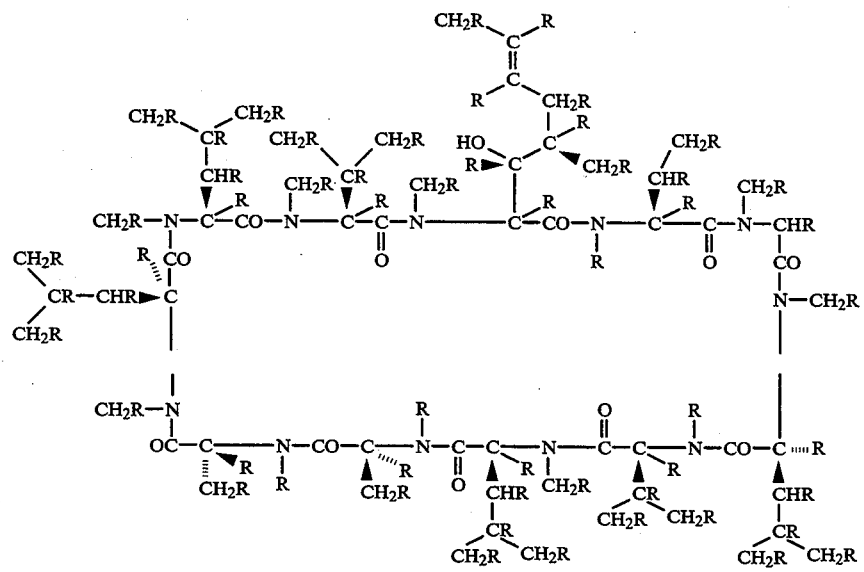

wherein each R may independently be H or X, provided that at least one R is X, where X is a ligand which is produced as the result of a photochemical reaction between a precursor of X containing a photochemically activatable group and a hydrogen of cyclosporine A and which comprises a reactive group.

The invention further provides that the reactive group may be a group which is reactive with a macromolecule. In a preferred embodiment of this invention, the macromolecule may be a polypeptide. In a very preferred embodiment, the invention further provides that the polypeptide may be a protein. In a preferred embodiment, the reactive group may be a carboxyl.

Specific examples of X may include but are not limited to the following:

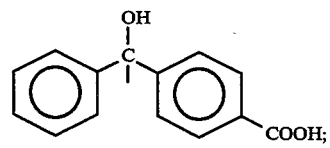

-continued

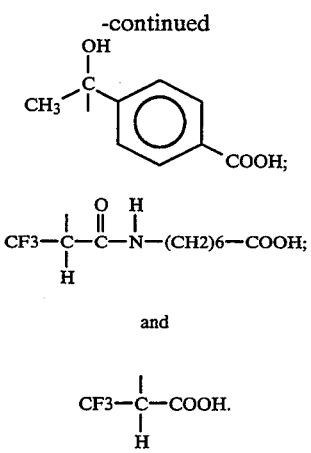

$$CF_3-\overset{O}{\overset{\|}{C}}-\overset{H}{\underset{H}{C}}-N-(CH_2)_6-COOH;$$

and $$CF_3-\underset{H}{C}-COOH.$$

In a preferred embodiment of the invention, the probability is greater than 0.75 that only one R in the aforementioned molecule is X. In a very preferred embodiment, the probability is about 1.0.

The present invention further provides a molecule which comprises a congener of cyclosporine A characterized by the structural backbone of cyclosporine A in which one or more hydrogen atoms are replaced by one or more ligands, each such ligand both comprising a reactive group and being attached to the structural backbone of cyclosporine A at a location which a hydrogen atom has been replaced as the result of a photochemical reaction between a precursor of the ligand containing a photochemically activatable group and the hydrogen atom being replaced.

The present invention further provides an immunosuppresive agent useful for preventing organ rejection in a transplant subject comprising an amount of the aforementioned molecules effective to inhibit organ rejection in a transplant subject and a pharmaceutically acceptable carrier.

The present invention also provides a composition of matter which comprises a conjugate of a compound and the aforementioned molecule wherein the compound is bound to the molecule through the reactive group of the ligand X.

The invention further provides a composition of matter which comprises a conjugate of a macromolecule and the aforementioned molecule wherein the macromolecule is bound to the molecule through the reactive group of the ligand X.

Similarly, the invention provides a composition of matter which comprises a conjugate of a polypeptide and the aforementioned molecule wherein the polypeptide is bound to the molecule through the reactive group of the ligand X.

Moreover, the invention provides a composition of matter which comprises a conjugate of a protein and the aforementioned molecule wherein the protein is bound to the molecule through the reactive group of the ligand X. Specific examples of this protein includes bovine serum albumin, rabbit serum albumin, keyhole limpet hemocyanin, ovalbumin, or any globulin including but not limited to thyroglobulin.

The invention also provides a method for preventing rejection in a transplant subject comprising administering to the subject an amount of the aforementioned molecule effective to inhibit organ rejection in the transplant subject.

The subject invention further provides an antibody directed to the aforementioned composition of matter specific for cyclosporine A or congener of cyclosporine A. In accordance with the teachings of the invention, the antibody may further be characterized as polyclonal or monoclonal. These antibodies may be detectably labeled.

The invention further provides a method of detecting the presence of cyclosporine A or congener of cyclosporine A in a biological tissue sample which comprises treating the biological tissue sample with the aforementioned detectably labeled antibody under conditions permitting the antibody to bind to cyclosporine A or congener and form a complex therewith, removing labeled antibody which is not bound to cyclosporine A or congener, detecting the presence of labeled antibody bound to cyclosporine A or congener and thereby detecting the presence of cyclosporine A or congener in the biological tissue sample.

The invention further provides another method of detecting the presence of cyclosporine A or a congener of cyclosporine A in a biological tissue sample which comprises treating the biological tissue sample with the aforementioned unlabeled antibody under conditions permitting the antibody to bind to cyclosporine A or congener and form a complex therewith, removing antibody which is not bound to cyclosporine A or congener, treating the complex with a labeled antibody directed to the unlabeled antibody under conditions such that the labeled antibody binds to the unlabeled antibody of the complex; removing labeled antibody which is not bound to the complex, detecting the presence of labeled antibody bound to the complex and thereby detecting the presence of cyclosporine A or congener in the biological tissue sample.

Additionally, this invention provides a method of determining the concentration of cyclosporine A or congener of cyclosporine A in a biological fluid sample which comprises, contacting a solid support with an excess of the aforementioned composition of matter under conditions permitting the composition of matter to attach to the surface of the solid support, contacting a predetermined volume of biological fluid sample with a predetermined amount of the aforementioned labeled antibody under conditions such that the cyclosporine A or congener in the sample binds to the labeled antibody and forms a complex therewith, contacting the resulting complex to the solid support to the surface of which the composition of matter is attached under conditions permitting the labeled antibody of the complex to bind to the composition of matter, treating the solid support so that only the composition of matter and labeled antibody of the complex bound thereto remain, quantitatively determining the amount of labeled antibody of the complex bound to the composition of matter, and thereby determining the concentration of cyclosporine A or congener in the biological fluid sample.

This invention provides another method of determining the concentration of cyclosporine A or congener of cyclosporine A in a biological fluid sample which comprises contacting a solid support with an excess of the aforementioned composition of matter under conditions permitting the composition of matter to attach to the surface of the solid support, contacting a predetermined volume of biological fluid sample with a predetermined amount of the aforementioned antibody under conditions such that the cyclosporine A or congener in the sample binds to the antibody and forms a complex therewith, contacting this complex with a predetermined amount of labeled antibody directed to the unlabeled antibody under conditions such that the labeled antibody binds to the unlabeled antibody complex of the prior step and forms a labeled complex therewith, contacting the resulting labeled complex to the solid support to the surface of which the composition of matter is attached under conditions permitting the unlabeled antibody bound to the labeled antibody of the labeled complex to bind to the composition of matter, treating the solid support so that only the composition of matter and labeled complex bound thereto remain, quantitatively determining the amount of labeled antibody of the labeled complex bound to the unlabeled antibody which is in turn bound to the composition of matter, and thereby determining the concentration of cyclosporine A or congener in the biological fluid sample.

In the two aforementioned methods of determining the concentration of cyclosporine A or congener, the composition of matter may be attached to the surface of the solid support by covalent or noncovalent bonds.

The invention also provides a method of determining the concentration of cyclosporine A or congener of cyclosporine A in a biological fluid sample by radioimmunoassay which comprises radioactively labeling a predetermined amount of a substance comprising cyclosporine A, congener of cyclosporine A or the aforementioned composition of matter, adding the predetermined amount of radiolabeled substance to the biological fluid sample, contacting this mixture with a predetermined amount of the aforementioned unlabeled antibody under conditions suitable to permit the antibody to bind to the cyclosporine A or congener in the biological fluid sample and the labeled substance, removing any unbound radiolabeled substance, quantitatively determining the amount of labeled substance bound to the antibody, and thereby determining the concentration of cyclosporine A or congener in the biological fluid sample.

The invention also provides a method of monitoring levels of cyclosporine A or congener of cyclosporine A in a subject which comprises taking biological fluid samples from a subject at predetermined intervals and determining the amount of cyclosporine A or congener in each biological fluid sample according to the aforementioned assays.

The aforementioned biological fluid may be, but is not limited to, blood, urine, feces or extracts of tissue.

The invention additionally provides a method for producing a monoclonal auto-anti-idiotypic antibody which comprises contacting lymphoid cells of an animal under suitable conditions with an effective antibody-raising amount of the aforementioned composition of matter, collecting the lymphoid cells at a suitable time after the contacting, fusing the collected lymphoid cells with appropriate myeloma cells to produce a series of hybridoma cells each of which produces a monoclonal antibody, screening under suitable conditions the series of hybridoma cells so produced to identify those which secrete a monoclonal antibody capable of binding to an antibody directed to the aforementioned composition of matter, separately culturing a hybridoma cell so identified in an appropriate medium, and separately recovering under suitable conditions the monoclonal anti-idiotypic antibody produced by the hybridoma cell.

The invention further provides an antibody directed to the aforementioned monoclonal auto-anti-idiotypic antibody. Additionally, the invention provides an antibody directed to the aforementioned antibodies. These antibodies directed to other antibodies may be used in an immunoregulatory substance useful for preventing organ rejection in a tranplant subject in an amount effective to inhibit organ rejection in a tranplant subject and a pharmaceutically acceptable carrier.

The invention further provides a method of reducing the amount of cyclosporine A or congener in a subject which comprises administering intravenously to the subject an amount of the aforementioned antibody effective to reduce the amount of cyclosporine A and permitting the antibody to bind to the excess cyclosporine A, thereby rendering the excess cyclosporine A ineffective.

The invention also provides a method of reducing the amount of endogenous immunoregulatory substances, or other biologically active substances which are endogenous, which share epitopes with cyclosporine A or congener of cyclosporine A in a subject which comprises administering intravenously to the subject an amount of aforementioned antibody or fragment thereof effective to reduce the amount of endogenous substances and permitting the antibody or fragment thereof to bind to the excess endogenous substances, thereby rendering the excess endogenous substances ineffective.

Finally, the invention provides a method of testing the potential of a pharmalogical agent as an immunoactive agent which comprises running an immunochemical assay competitive between the pharmalogical agent and known amounts of labeled cyclosporine A or congener of cyclosporine A with the aforementioned antibody under conditions such that the antibody forms complexes with the pharmalogical agent and cyclosporine A or congener and determining the displacement from the antibody of labeled cyclosporine A or congener by the pharmalogical agent.

DETAILED DESCRIPTION OF THE INVENTION

Figure 1:
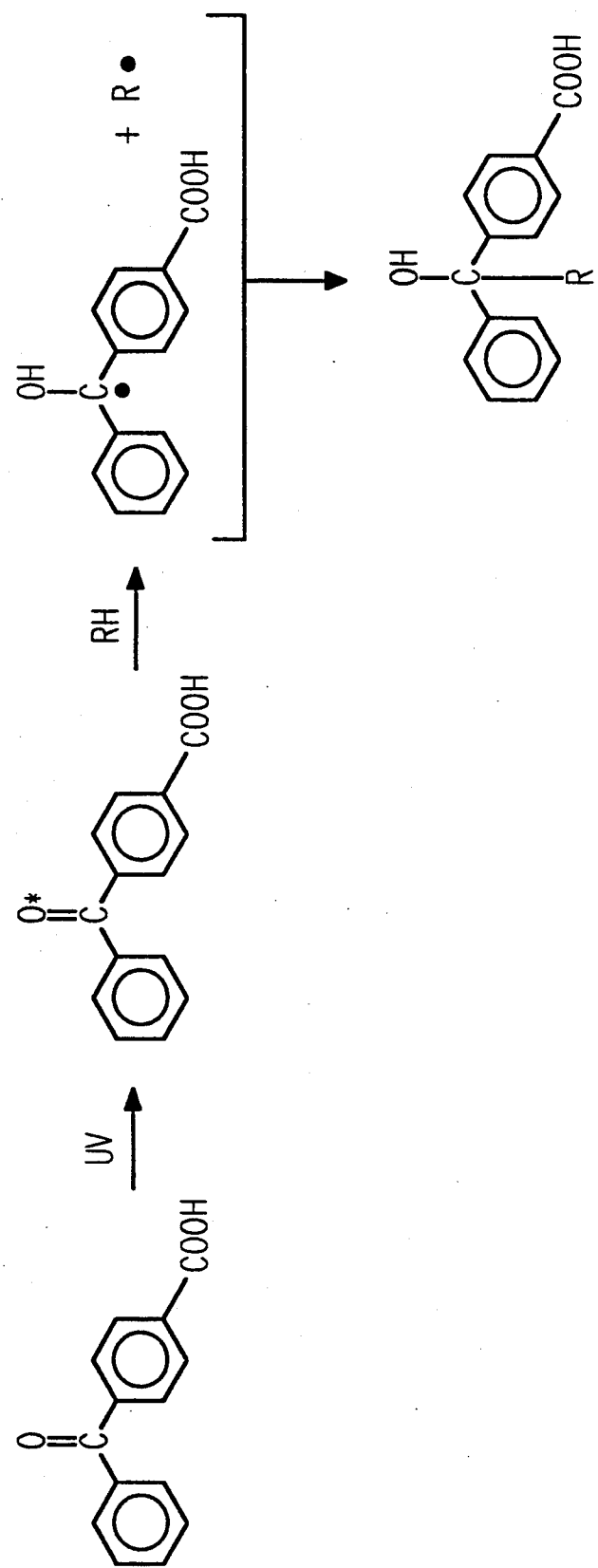
FIG. 1 shows the photochemical reaction between CsA and BBA.

The present invention provides a molecule having the structure:

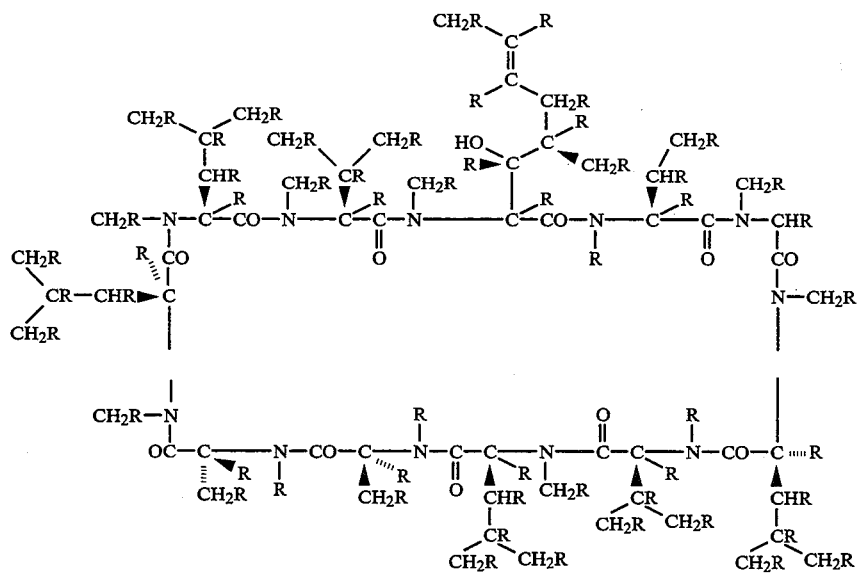

wherein each R may independently be H or X, provided that at least one R is X, where X is a ligand which is produced as the result of a photochemical reaction between a precursor of X containing a photochemically activatable group and a hydrogen of cyclosporine A and which comprises a reactive group.

The invention further provides that the reactive group may be a group which is reactive with a macromolecule. Examples of such macromolecules include, but are not limited to, polysaccharides, complex carbohydrates, and any organic polymers including but not limited to polyacrilimide, polynitrocellulose, and polystyrene. In a preferred embodiment of this invention, the macromolecule may be a polypeptide. In a very preferred embodiment, the invention further provides that the polypeptide may be a protein.

In a further embodiment of the invention, the reactive group may be an ester, carbamyl, amine or phosphonamide. In a preferred embodiment, the reactive group may be a carboxyl.

Photochemical reactions are well known in the art (7) and it is to be understood that X may be any ligand which is produced as the result of a photochemical reaction between a precursor of X containing a photochemically activatable group and a hydrogen of cyclosporine A and which comprises a reactive group. Specific examples of X may include but are not limited to the following:

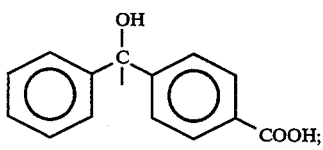

-continued

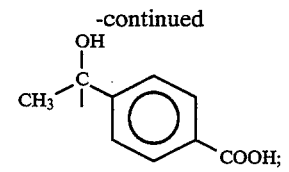

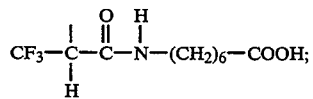

and

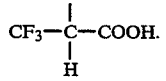

In a preferred embodiment of the invention, the probability is greater than 0.75 that only one R in the aforementioned molecule is X. In a very preferred embodiment, the probability is about 1.0.

The present invention further provides a molecule which comprises a congener of cyclosporine A characterized by the structural backbone of cyclosporine A in which one or more hydrogen atoms are replaced by one or more ligands, each such ligand both comprising a reactive group and being attached to the structural backbone of cyclosporine A at a location which a hydrogen atom has been replaced as the result of a photochemical reaction between a precursor of the ligand containing a photochemically activatable group and the hydrogen atom being replaced.

Congeners of cyclosporine A currently exist in the literature (5, 8) and it is anticipated that many more may be developed. It is foreseen that the novelties of the subject application which are applicable to cyclosporine A may also be applicable to such congeners. The basic structure of cyclosporine A is as follows:

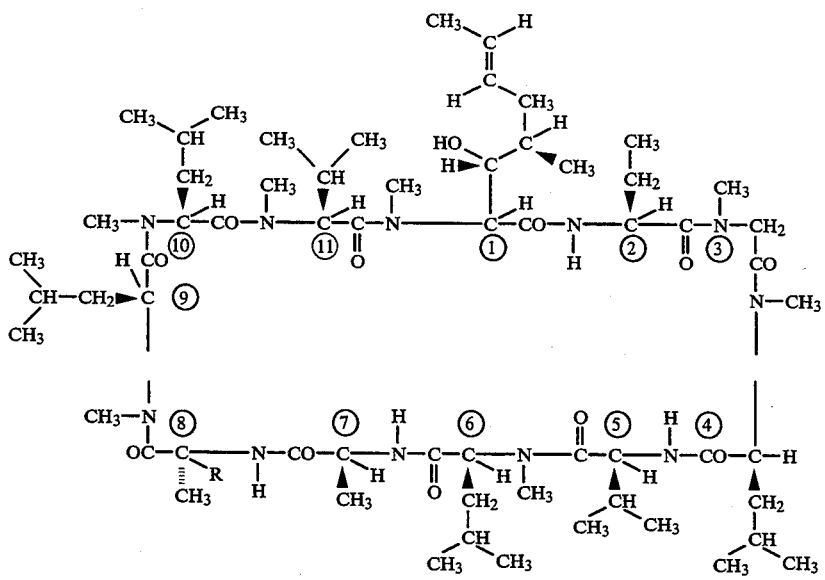

Examples of such congeners include, but are not limited to, cyclosporine A with:
(a) alanine at position 2;
(b) threonine at position 2;
(c) valine at position 2;
(d) norvaline at position 2 and 5; and
(e) alphaamino butyric acid at position 7.

The present invention further provides an immunosuppresive agent useful for preventing organ rejection in a transplant subject comprising an amount of the aforementioned molecules effective to inhibit organ rejection in a transplant subject and a pharmaceutically acceptable carrier.

As used herein, the term "pharmaceutically acceptable carrier" encompasses any of the standard pharmaceutical carriers. Such carriers are well known in the art and may include, but are not intended to be limited to, any of the standard pharmaceutical carriers such as phosphate buffered saline solution, water, emulsions such as oil/water emulsion, and various types of wetting agents.

The aforementioned immunosuppresive compositions may be superior to cyclosporine A in several ways. First, the compositions may avoid the toxicity problems inherent with cyclosporine A, specifically kidney damage. Second, these compositions may be soluble and thereby preferable for dosage regulation.

The present invention also provides a composition of matter which comprises a conjugate of a compound and the aforementioned molecule wherein the compound is bound to the molecule through the reactive group of the ligand X. The general process for preparation of antigenic hapten-carrier conjugates is known in the art (9).

The invention further provides a composition of matter which comprises a conjugate of a macromolecule and the aforementioned molecule wherein the macromolecule is bound to the molecule through the reactive group of the ligand X.

Similarly, the invention provides a composition of matter which comprises a conjugate of a polypeptide and the aforementioned molecule wherein the polypeptide is bound to the molecule through the reactive group of the ligand X.

Moreover, the invention provides a composition of matter which comprises a conjugate of a protein and the aforementioned molecule wherein the protein is bound to the molecule through the reactive group of the ligand X. Again, it is to be understood that the scope of the invention includes any protein capable of being bound to the molecule. Specific examples of this protein includes bovine serum albumin, rabbit serum albumin, keyhole limpet hemocyanin, ovalbumin, or any globulin including but not limited to thyroglobulin.

The invention also provides a method for preventing rejection in a transplant subject comprising administering to the subject an amount of the aforementioned molecule effective to inhibit organ rejection in the transplant subject.

The subject invention further provides an antibody directed to the aforementioned composition of matter specific for cyclosporine A or congener of cyclosporine A. In accordance with the teachings of the invention, the antibody may further be characterized as polyclonal or monoclonal.

These antibodies may be detectably labeled. Such labels are well known in the art and include but are not limited to enzyme labels and radioactive labels such as fluorophore or biotinylated labels.

The invention further provides a method of detecting the presence of cyclosporine A or congener of cyclosporine A in a biological tissue sample which comprises treating the biological tissue sample with the aforementioned detectably labeled antibody under conditions permitting the antibody to bind to cyclosporine A or congener and form a complex therewith, removing labeled antibody which is not bound to cyclosporine A or congener, detecting the presence of labeled antibody bound to cyclosporine A or congener and thereby detecting the presence of cyclosporine A or congener in the biological tissue sample.

The invention further provides another method of detecting the presence of cyclosporine A or a congener of cyclosporine A in a biological tissue sample which comprises treating the biological tissue sample with the aforementioned unlabeled antibody under conditions permitting the antibody to bind to cyclosporine A or congener and form a complex therewith, removing antibody which is not bound to cyclosporine A or congener, treating the complex with a labeled antibody directed to the unlabeled antibody under conditions such that the labeled antibody binds to the unlabeled antibody of the complex, removing labeled antibody which is not bound to the complex, detecting the presence of labeled antibody bound to the complex and thereby detecting the presence of cyclosporine A or congener in the biological tissue sample.

Detecting the presence of cyclosporine A or congener in biological tissue sample is useful since the toxic effects of cyclosporine A include damage to tissues, particularly kidney. Accordingly, in a preferred embodiment of the method of detecting the presence of cyclosporine A or congener, the biological tissue sample is kidney.

Additionally, this invention provides a method of determining the concentration of cyclosporine A or congener of cyclosporine A in a biological fluid sample which comprises, contacting a solid support with an excess of the aforementioned composition of matter under conditions permitting the composition of matter to attach to the surface of the solid support, contacting a predetermined volume of biological fluid sample with a predetermined amount of the aforementioned labeled antibody under conditions such that the cyclosporine A or congener in the sample binds to the labeled antibody and forms a complex therewith, contacting the resulting complex to the solid support to the surface of which the composition of matter is attached under conditions permitting the labeled antibody of the complex to bind to the composition of matter, treating the solid support so that only the composition of matter and labeled antibody of the complex bound thereto remain, quantitatively determining the amount of labeled antibody of the complex bound to the composition of matter, and thereby determining the concentration of cyclosporine A or conger in the biological fluid sample.

This invention provides another method of determining the concentration of cyclosporine A or congener of cyclosporine A in a biological fluid sample which comprises contacting a solid support with an excess of the aforementioned composition of matter under conditions permitting the composition of matter to attach to the surface of the solid support, contacting a predetermined volume of biological fluid sample with a predetermined amount of the aforementioned antibody under conditions such that the cyclosporine A or congener in the sample binds to the antibody and forms a complex therewith, contacting this complex with a predetermined amount of labeled antibody directed to the unlabeled antibody under conditions such that the labeled antibody binds to the unlabeled antibody complex of the prior step and forms a labeled complex therewith, contacting the resulting labeled complex to the solid support to the surface of which the composition of matter is attached under conditions permitting the unlabeled antibody bound to the labeled antibody of the labeled complex to bind to the composition of matter, treating the solid support so that only the composition of matter and labeled complex bound thereto remain, quantitatively determining the amount of labeled antibody of the labeled complex bound to the unlabeled antibody which is in turn bound to the composition of matter, and thereby determining the concentration of cyclosporine A or congener in the biological fluid sample.

In the two aforementioned methods of determining the concentration of cyclosporine A or congener, the composition of matter may be attached to the surface of the plate by covalent or noncovalent bonds.

The invention also provides a method of determining the concentration of cyclosporine A or congener of cyclosporine A in a biological fluid sample by radioimmunoassay which comprises radioactively labeling a predetermined amount of a substance comprising cyclosporine A, congener of cyclosporine A or the aforementioned composition of matter, adding the predetermined amount of radiolabeled substance to the biological fluid sample, contacting this mixture with a predetermined amount of the aforementioned unlabeled antibody under conditions suitable to permit the antibody to bind to the cyclosporine A or congener in the biological fluid sample and the labeled substance, removing any unbound radiolabeled substance, quantitatively determining the amount of labeled substance bound to the antibody, and thereby determining the concentration of cyclosporine A or congener in the biological fluid sample.

Methods of determining the concentration of cyclosporine A or congener in the biological fluid sample from data concerning labeled complex is well known in the art. One such example includes comparing the data to a standard curve.

It is to be understood that it is within the scope of the present invention to use other types of assays with the afomentioned antibodies for determining the concentration of cyclosporine A in a biological fluid sample.

The invention also provides a method of monitoring levels of cyclosporine A or congener of cyclosporine A in a subject which comprises taking biological fluid samples from a subject at predetermined intervals and determining the amount of cyclosporine A or congener in each biological fluid sample according to the aforementioned assays.

The aforementioned biological fluid may be, but is not limited to, blood, urine, feces or extracts of tissue.

The invention additionally provides a method for producing a monoclonal auto-anti-idiotypic antibody which comprises contacting lymphoid cells of an animal under suitable conditions with an effective antibody-raising amount of the aforementioned composition of matter, collecting the lymphoid cells at a suitable time after the contacting, fusing the collected lymphoid cells with appropriate myeloma cells to produce a series of hybridoma cells each of which produces a monoclonal antibody, screening under suitable conditions the series of hybridoma cells so produced to identify those which secrete a monoclonal antibody capable of binding to an antibody directed to the aforementioned composition of matter, separately culturing a hybridoma cell so identified in an appropriate medium, and separately recovering under suitable conditions the monoclonal anti-idiotypic antibody produced by the hybridoma cell. Methods of producing monoclonal auto-anti-idiotypic antibodies are previously known in the art as outlined in co-pending patent application U.S. Serial No. 273,654, filed Nov. 18, 1988, continuation of U.S. Ser. No. 767,516, filed Aug. 20, 1985.

The invention further provides an antibody directed to the aforementioned monoclonal auto-anti-idiotypic antibody. Additionally, the invention provides an antibody directed to the aforementioned antibodies. These antibodies directed to other antibodies may be used in an immunoregulatory substance useful for preventing organ rejection in a tranplant subject in an amount effective to inhibit organ rejection in a tranplant subject and a pharmaceutically acceptable carrier.

The invention further provides a method of reducing the amount of cyclosporine A or congener in a subject which comprises administering intravenously to the subject an amount of the aforementioned antibody effective to reduce the amount of cyclosporine A and permitting the antibody to bind to the excess cyclosporine A, thereby rendering the excess cyclosporine A ineffective.

The invention also provides a method of reducing the amount of endogenous immunoregulatory substances, or other biologically active substances which are endogenous, which share epitopes with cyclosporine A or congener of cyclosporine A in a subject which comprises administering intravenously to the subject an amount of aforementioned antibody or fragment thereof effective to reduce the amount of endogenous substances and permitting the antibody or fragment thereof to bind to the excess endogenous substances, thereby rendering the excess endogenous substances ineffective.

Finally, the invention provides a method of testing the potential of a pharmalogical agent as an immunoactive agent which comprises running an immunochemical assay competitive between the pharmalogical agent and known amounts of labeled cyclosporine A or congener of cyclosporine A with the aforementioned antibody under conditions such that the antibody forms complexes with the pharmalogical agent and cyclosporine A or congener and determining the displacement from the antibody of labeled cyclosporine A or congener by the pharmalogical agent.

This invention is illustrated in the Experimental Details section which follows. This section is set forth to and in an understanding of the invention but is not intended to, and should not be construed to, limit in any way the invention as set forth in the claims which follow thereafter.

Experimental Details

EXAMPLE I

Materials and Methods

4-Benzyoylbenzoic acid (BBa) was purchased from Aldrich Chemicals. Bovine and rabbit serum albumin (BSA and RSA) and N-hydroxysuccinimide were from Sigma Chemical. Dicyclohexylcarbodiimide was from Fluka. Cyclosporin A (CsA), [$^3$H]CsA (50Ci/mMole), Cyclosporin "RIA-kits" and the various modified derivatives were generous gifts from Sandoz Ltd., Basel, Switerland. [$^3$H]CsA (17Ci/mMole) was purchased from Amersham. Kieselgel (silica gel 60 F254) was purchased from E. Merck (cat. no. 5766).

Photolysis reaction

CsA (104 mg, 83 $\mu$moles) was mixed with 36 mg (160 $\mu$moles) of BBa in 0.6 ml of benzene. The solution was purged with nitrogen gas and photolysed at 320nm with a Spectroline B100 UV lamp (Spectronics, Westbury, L.I.) for 7 hours at a distance of 8 cm, at room temperature. Approximately 1 microcurie of [$^3$H] dihydro CsA was added as a tracer prior to exposure to UV. After photolysis, the benzene was evaporated in a rotating still in vacuo and the dried product dissolved in 1.5 ml of methanol. The product was isolated by preparative thin layer chromatography on silica gel, in a solvent system of CHCl$_3$/methanol (85/15). Two major bands were seen: Rf=0.58 and 0.72. The slower moving band (i.e. the product of the reaction, CsA-BBa) was eluted with methanol, and counted for radioactivity.

Hapten-Protein Conjugates

CsA-BBa (5.5 mg, ca. 4 $\mu$moles) was added to 1 ml solution containing 552 $\mu$g (4.8 $\mu$moles) of N-hydroxysuccinimide (NHS) and 825 $\mu$g (4 $\mu$moles) of dicyclohexylcarbodiimide in 1 ml of methanol. The reaction was allowed to run overnight at room temperature and ester formation was detected with a neutral Fe-hydroxamate test (10-11).

Carrier proteins (BSA or RSA) (10 mg; 0.14 $\mu$mole) were dissolved in 1.0 ml of distilled H$_2$O, and the pH adjusted to 9.0 with M Na$_2$CO$_3$. CsA-BBa-NHS (5.2 mg; 3.6 $\mu$moles) in 1.0 ml of methanol was added dropwise to the protein solution. After all was added, the pH was readjusted to 9 and the reaction allowed to proceed overnight at room temperature. The reaction mixture was then dialyzed against PBS for 24 hours and counted for radioactivity to determine coupling efficiency. About 6-7 cyclosporins were coupled to each molecule of BSA or RSA. The conjugates were further purified by gel filtration HPLC (LKB TSK 3000). Confirmation of the linkage of CsA to the proteins came from RIA inhibition experiments. Quantitation is not possible by this technique because there was no way to determine the valence of the conjugate as a competitive inhibitor, i.e., how many of the haptens linked to the protein took part in the inhibition reaction.

Immunization

Two female New Zealand White rabbits were immunized intradermally along with the back, with a 1:1 (v:v) mixture of CsA-BBa-BSA in complete Freund's adjuvant (1 mg/ml of antigen). The rabbits were boosted with CsA-BBa-BSA in incomplete Freund's adjuvant at 3-4 week intervals and bled weekly following each boost. Both rabbits responded by producing cyclosporine-specific antibodies. The sera of one rabbit, R575, was characterized further.

Radioimmunoassay

Serum antibodies were detected by a modification of the published radioimmunoassay (5, 12). Serum (100 $\mu$l) diluted in Sandoz buffer A (50 mM Tris, pH 8.5) was added to 200 $\mu$l of [$^3$H]CsA in Sandoz buffer B (50 mM Tris, pH 8.5; 0.1% Tween 20) containing 2% horse serum, and incubated for 2 hours at room temperature or overnight at 4° C. Binding by diluted preimmune serum was used as a control. Free and bound ligand were separated with charcoal supplied by Sandoz according to their procedure.

Determination of antibody specificity

Antibody specificity was determined by an inhibition RIA, using a panel of six CsA analogues, modified at different amino acid positions. The cyclosporin derivatives were dissolved in 100% ethanol at a concentration of 5.0 mg/ml, stored at −20° C, and diluted to final concentrations of 0.27 nM to 2.7 $\mu$M in Sandoz buffer B for the inhibition experiments. A constant dilution of rabbit antibody, in buffer A, was added to 200 $\mu$l of buffer B containing [$^3$H] dihydro CsA and different amounts of inhibitor, and incubated overnight at 4° C. Inhibition curves for each CsA derivative were generated.

Detection of CsA in sera of transplant patients

Cyclosporin levels in the sera of 25 transplant patients were determined by an inhibition RIA, using either our rabbit anticyclosporin antibodies diluted 1:600 or a polyclonal antibody preparation supplied by Sandoz, as part of their kit. Diluted rabbit anticyclosporin antiserum (100 μl) or Sandoz polyclonal antibody were added to 100 μl [$^3$H]CsA in buffer B and 100 μl of patient's serum prediluted either 1:5 (for Sandoz antibody) or 1:15 (for our rabbit antibody) in buffer B, containing 2% horse serum. Sera from three different patients, taken before they had begun cyclosporin treatment, were used as controls. Samples were incubated overnight at 4° C., and CsA levels were calculated by comparing the level of inhibition to a standard curve obtained with known amounts of cyclosporin.

Scatchard Analysis

The binding constant of the rabbit antibodies was determined by Scatchard analysis. Different concentrations of [$^3$H] dihydro CsA, ranging from 10 nM to 0.1 nM, were added to a constant amount of antibody and allowed to incubate overnight at 4° C., bound ligand was determined by the RIA described above.

Results

CsA lacks chemically active groups that can be used for conjugation to proteins. Therefore, a novel procedure was developed for the purpose of introducing carboxyl groups into the molecule. This procedure, photochemical in nature, inserts a carboxyl-containing molecule (BBa) into the alkyl side chains of CsA (FIG. 1), presumably but not certainly, at random.

Figure 2:
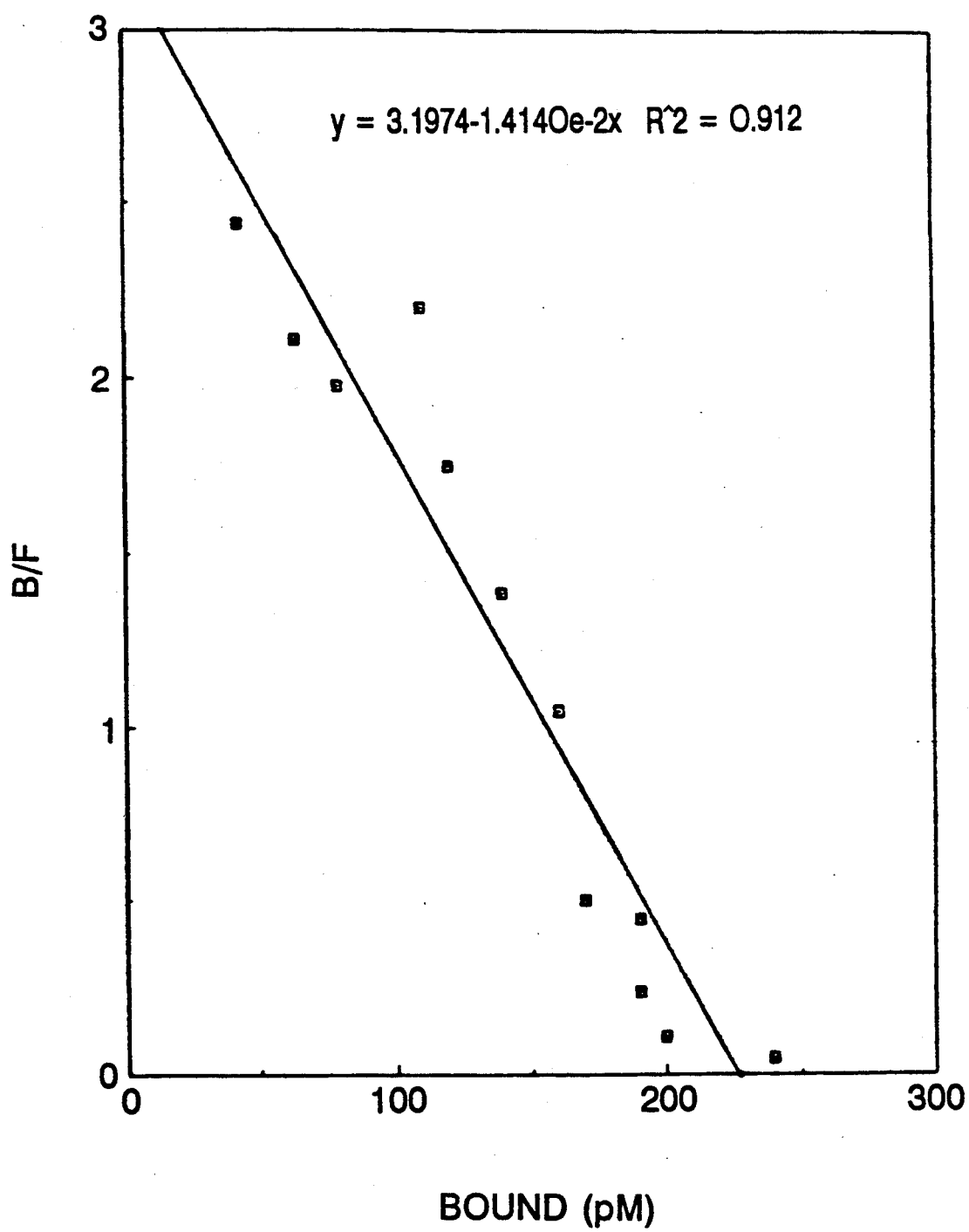
FIG. 2 shows the Scatchard plot of binding data.

Antibodies generated in rabbits with the CsA-BBa-BSA conjugate were examined for specificity and affinity by RIA. Scatchard analysis (FIG. 2) revealed a relatively homogenous population of high affinity antibodies, with Kd=9.8 ±2.8×10$^{-11}$M.

Figure 3:
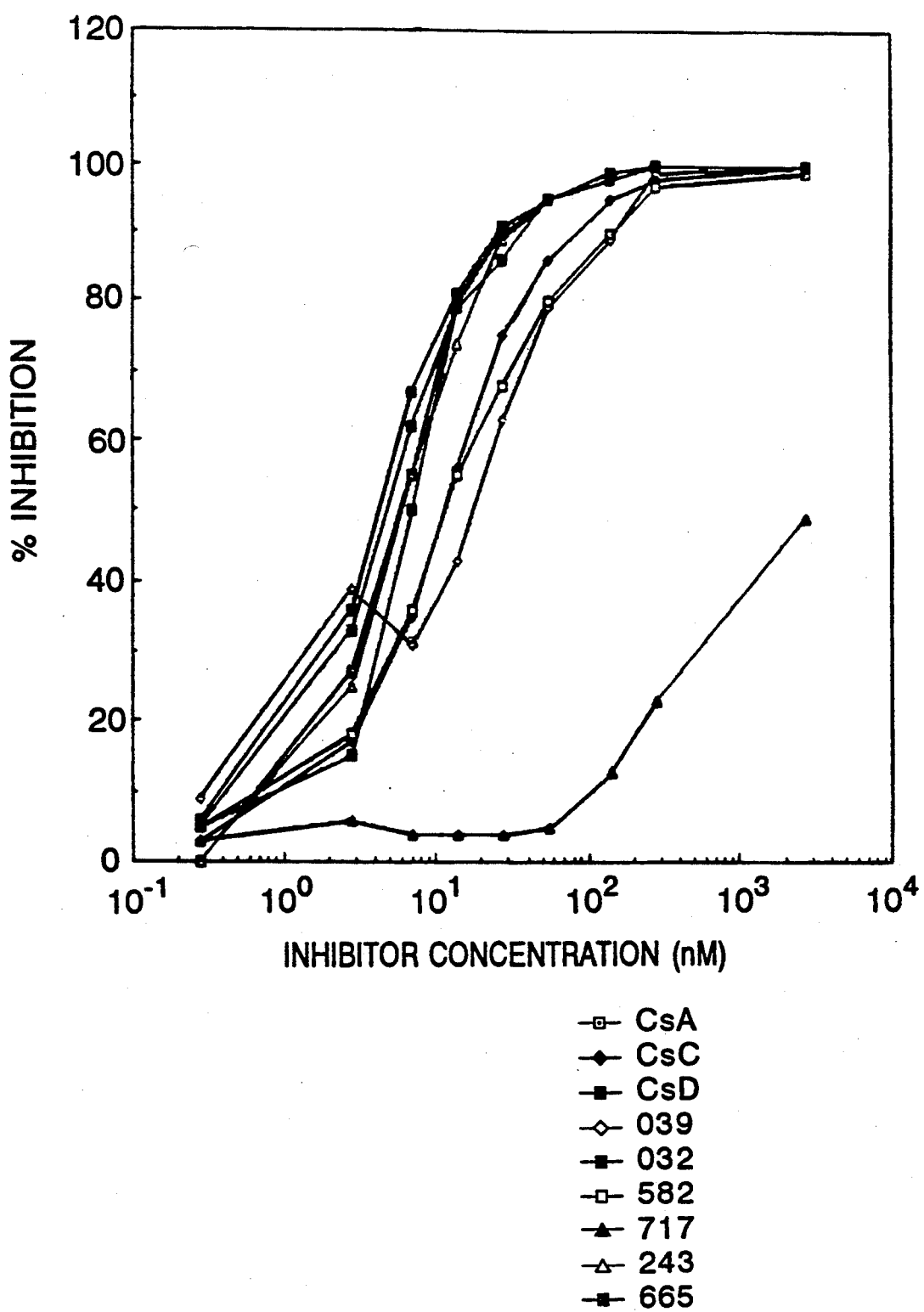
FIG. 3 shows the inhibition of the binding of CsA to R575 by various cyclosporine derivatives.

The specificity of the antibodies for various cyclosporin derivatives was determined by an inhibition RIA. The results are shown in FIG. 3 and Table I. The derivatives can be divided roughly into three groups according to their affinities: CsA, CsD, 665, 243 and 032 are in the high affinity group. CsC, 582 and 039 are of moderate affinities; 717 inhibits very poorly.

Figure 4:
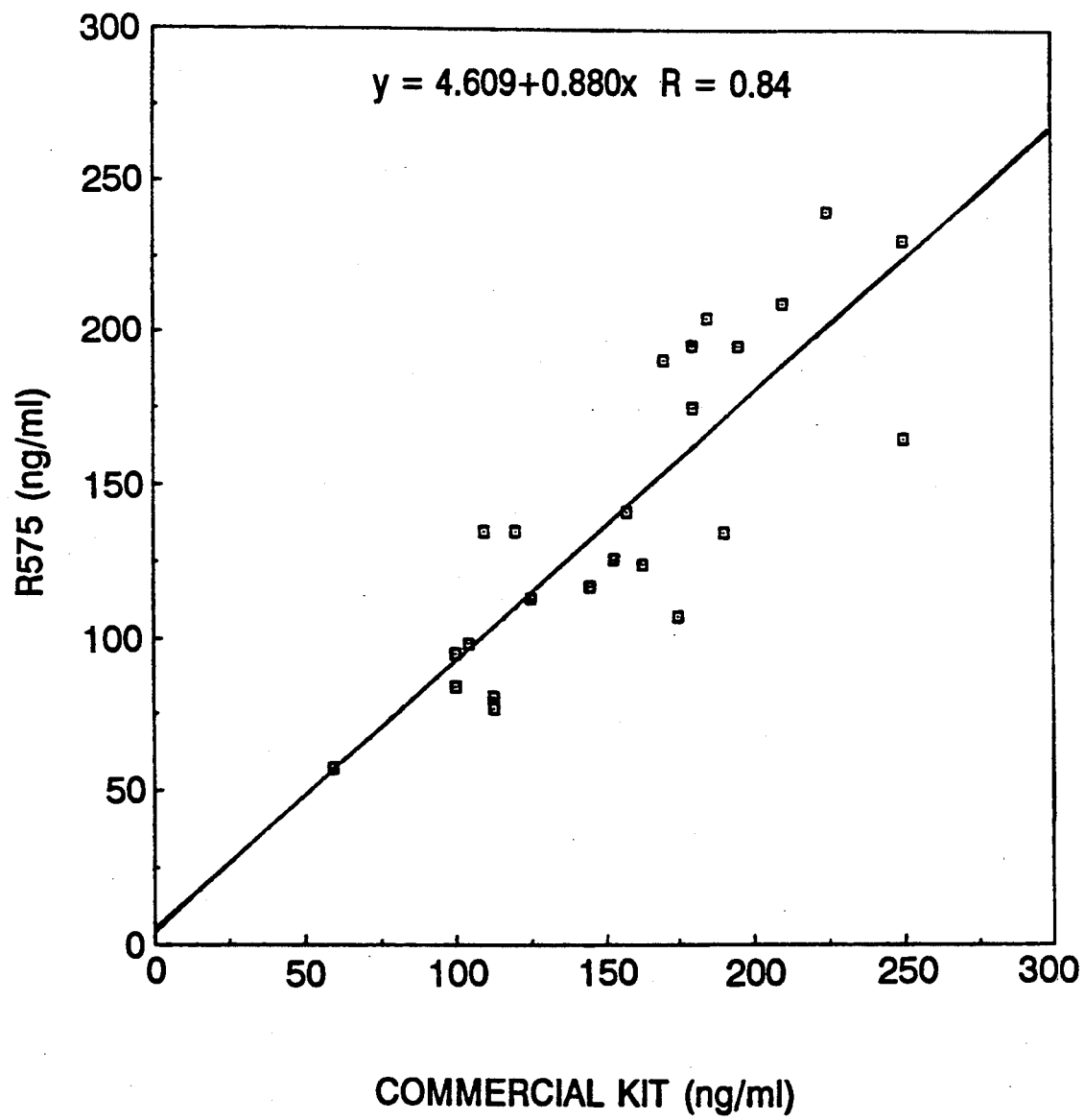
FIG. 4 shows the titers (ng/ml) of patients' sera as determined by RIA using R575 and Sandoz antibody.

Shown in Table II are the results of assays of cyclosporin levels in the sera of patients undergoing CsA treatment subsequent to cardiac transplantation. Titers were determined using our antibodies and the polyclonal antibodies in the Sandoz kit. Also tabulated in Table II are data supplied by the laboratory of the Department of Surgery. As illustrated in FIG. 4, in our hands the levels determined with our antibody agreed with results using the commercial kit. Linear regression analysis of the data yields a slope of 0.88 and a correlation coefficient of 0.84.

Discussion

The α, β unsaturated ketone, BBa, is among reagents that, upon photoactivation by U.V. light, can insert into alphatic side chains (7). It was selected for this study because its photoactive intermediate does not cleave peptide bonds (13). This is an important consideration because it has been shown that a single break in a peptide bond of CsA, such as in iso-CsA, which has lost a peptide bond by an N O shift, leads to loss of activity even though, in the case of Iso-CsA, a cyclic structure is maintained. Apparently an altered conformation leads to a biologically inactive molecule.

The insertion of BBa into CsA is probably a somewhat random process, although we have not attempted to characterize the various products. If random, we are generating populations of antibodies that recognize different residues of the CsA molecule. We have tried to learn something about these antibodies by doing inhibition studies with a panel of cyclosporin derivatives (FIG. 3, Table I). First of all, the relatively shallow slopes of the curves indicate that the immune response is oligo or polyclonal, probably the former. If it were monoclonal 90% inhibition would occur at a tenfold higher concentration than 10% inhibition. A second important observation is that 100% inhibition of [$^3$H] CsA binding can be obtained with all of the competing

TABLE 1

| IC$_{50}$[a] of Various Analogues of CsA | |
|---|---|
| Derivative[b] | IC$_{50}$ (nM) |
| CsD | 4.3 |
| 665 | 4.8 |
| A | 6.0 |
| 243 | 6.0 |
| 032 | 7.0 |
| CsC | 11.5 |
| 582 | 12.0 |
| 039 | 18.0 |
| 717 | 2700 |

[a]IC$_{50}$ = Concentration for 50% inhibition
[b]The derivatives listed differ from CsA in the following ways:
CsD, valine replaces α-aminobutyric acid at position 2;
665, O-acetylthreonine replaces α-aminobutyric acid at position 2;
243, hydroxyl group of (4R)-4-[(E)-2-butenyl]-4-N-dimethyl-L-threonine in position 1 is acetylated;
032, N-methylisoleucine replaces N-methylvaline at position 11;
CsC, threonine replaces α-aminobutyric acid at position 2;
582, proline replaces sarcosine at position 3;
039, N-methyl-D-alanine N-methylleucine at position 6;
717, O-t-butyl-D-serine replaces D-alanine at position 8.

TABLE 2

| Cyclosporine Titers in Patients' Sera (ng/ml) | | | |
|---|---|---|---|
| Patient # | R575[a] | Commercial[b] | Hospital Laboratory[c] |
| 1 | 51 | undetectable | 30 |
| 2 | 190 | 170 | 128 |
| 3 | 195 | 180 | 156 |
| 4 | 135 | 120 | 76 |
| 5 | 175 | 180 | 180 |
| 6 | 135 | 110 | 88 |
| 7 | 195 | 195 | 164 |
| 8 | 205 | 185 | 172 |
| 9 | 240 | 225 | 245 |
| 10 | 210 | 210 | 215 |
| 11 | 113 | 125 | 180 |
| 12 | 95 | 100 | 124 |
| 13 | 77 | 113 | 124 |
| 14 | 98 | 105 | 88 |
| 15 | 84 | 100 | 112 |
| 16 | 124 | 163 | 152 |
| 17 | 165 | 250 | 205 |
| 18 | 135 | 190 | 180 |
| 19 | 141 | 158 | 132 |
| 20 | 231 | 250 | 188 |
| 21 | 126 | 153 | 134 |
| 22 | 81 | 113 | 88 |
| 23 | 117 | 145 | 110 |
| 24 | 107 | 175 | 148 |
| 25 | 57 | 60 | 71 |

[a]Antibody prepared according to details of this paper.
[b]Antibody in kit from Sandoz Ltd. Assay run in our laboratory.
[c]Results reported by hospital laboratory using Sandoz kit.

cyclosporin derivatives except 717, which, however, is certainly capable of more than 50% inhibition. These results indicate that all of the cyclosporin derivatives compete for the total population of antibodies specific for CsA.

The inhibition data in Table I and FIG. 3 indicate that the various cyclosporine derivatives can be divided into three groups with respect to their affinities for the population of antibodies in the immune sera. CsA, CsD, 665, 243 and 032 bind best. Moderate affinities are shown by CsC, 582 and 039. The results with 717 indicate low affinity. Derivative 717 differs from CsA by having a bulky O-t-butyl-D-serine instead of D-alanine at position 8. This could implicate position 8 as a dominant epitope. On the other hand, introduction of a bulky group at position 8, in place of the compact methyl group of D-alanine, could distort the cyclosporine molecule markedly (6).

The derivatives showing moderate affinities, CsC, 582 and 039, are substituted at position 2, 3 and 6 respectively. None of the substitutions are bulky. However, the substitution of proline for sarcosine at position 3 is known to disturb the conformation of 582 at positions 3 and 4 (14).

Those derivatives having affinities similar to that of CsA are substituted in positions 1, 2 and 11, all clustered at one "face" of the cyclic peptide. The substitutions, however, are not drastic with respect to size differences of the side chains. A definitive study of the specificity of the antisera and correlation with conformation and biological activity requires testing with a larger number of cyclosporin analogues, which are available (14).

Assay of cyclosporin levels in patients' sera is feasible with this antibody preparation. Our results (FIG. 4 and Table II) are in good agreement with cyclosporin levels determined using commercial (Sandoz) antisera prepared by immunization with a protein conjugate of CsC. The moderate discrepancies probably indicate differences in cross specificities of the antibodies for metabolites of cyclosporine, (5), which is to be expected since our antigen differs from the antigen used to produce the commercial antiserum.

EXAMPLE II

Preparation of CyA-BSA Conjugate and CyA-Sepharose Affinity Column

The character of the side chains of CyA (i.e., an absence of amino or carboxyl groups) precluded the use of conventional coupling procedures, except possibly to the unusual "C-9-amino acid" in position 1(N-methyl-(4R)-4-butenyl-(L)-threonine) (15–17). However, modification of this amino acid was ill advised since this residue was critical to the biological activity of CyA. CyC has threonine instead of γ-aminobutyric acid at the second amino acid position (AA2). This analog is biologically active and has been used to prepare cyclosporine-protein conjugates using the hemisuccinate derivative (15, 5). As noted by Kahan, however, coupling to this residue was likely to lead to steric interference with the "active" portion of the molecule (18). This conclusion was based on substitution studies in which it had been shown that amino acids 11, 1, 2, and 3 were critical for imunosuppressive activity (17). Because of this possibility, we used a photochemical procedure that has provided random links to the various exposed methyl or methylene groups of Cya. By having populations of CyA derivatives heterogeneous with regard to attachment sites, it was insured that a portion of the molecules could be coupled to protein without the active amino acids being buried.

We first reacted p-nitrophenyl-2-diazo-3,3,3-trifluoropropionate (19, 20) with a large excess of aminohexanoic acid in andhydrous dimethyl formamide. The reaction mixture was incubated in the dark at room temperature for 18 hours, following a similar procedure described by Samuels and coworkers (21). The product was isolated by preparative TLC (21) and has the following formula:

$$\overset{N}{\phantom{x}}\ \ \overset{O}{\phantom{x}}\ \ \overset{H}{\phantom{x}}$$
$$CF_3-C-C-N-(CH_2)_6-COOH.$$

Next CyA, which is very soluble in all organic solvents except hexane (17), was mixed with the above product in a benzene solvent and photolyzed. Two moles of carbene precursor to one mole cyclosporine A were also used. The mixture was irradiated with UV light from a mercury arc (mainly 254 nm). Reaction conditions were empirically chosen to avoid multiple substitutions of CyA molecules. Derivatized CyA (CyA-Hex) were separated by TLC. To provide a functional group that reacted with amino groups, the carboxyl group(s) of CyA-Hex were activated by conversion to the N-hydroxy succinimide (NHS) ester in the presence of dicyclohexylcarbodiimide. Then, CyA-Hex-NHS was dissolved in anhydrous dimethyl formamide and added as a small volume to bovine albumin and keyholelimpet hemocyanin in pH=8.8 bicarbonate buffer and incubated overnight at 4° C. These conditions have been found to work well with other NHS derivatives (22, 23). To determine the degree of substitution of protein amino acid groups by CyA-Hex, we used the trinitrobenzene sulfonic acid procedure of Habeeb (24). In our previous studies, BSA and KLH conjugates were both found to work well as immunogens and as antigens in solid phase immunoassays. All chemicals needed for the preparation of these reagents were commercially available.

To prepare a CyA affinity column, an excess of CyA-Hex-NHS in anhydrous dimethyl foramide was reacted with aminohexyl-Sepharose 4B (AH-Sepharose 4B ®), suspended and swollen in the same solvent. This matrix, which was prepared by a carbonyldiimidazole coupling procedure, avoided the introduction of the ion exchange groups associated with the frequently used cyanogen bromide coupling and reduced leakage due to the crosslinked agarose and the stable carbonyldiimidazole linkage (25). Trinitrobenzene sulfonic acid will be used to get a semiquantitative estimate of residual amino groups on Sepharose beads.

References

1. Borel, J. F. (1981) Cyclosporin-A —Present experimental status. Transplant Proc. 13, 344.

2. Borel, J. F. (Ed.) (1986) Cyclosporin-A: Progr. Allergy 38, 474 pp.

3. Beveridge, T. (1983) Cyclosporin-A: An evaluation of clinical results. Transplantation Proceed. 15, 433.

4. Shaw, L. M., Bowers, L., Demers, L., Freeman, D., Moyer, T., Sanghvi, A., Sellman, H. (1987) Critical Issues in Cyclosporine Monitoring: Report of the Task Force on Cyclosporine Monitoring. Clin. Chem. 33, 1269.

5. Donatsch, P., Abisch, E., Homberger, M., Traber, R., Trapp, M and Voges, R. (1981) A radioimmunoassay to measure cyclosporin A in plasma and serum samples. J. Immunoassay 2, 19.

6. Quesniaux, V. F. J., Tees, R., Schrier, M. H., Wenger, R. M., Donatsch, P. and Van Regenmortel, M. H. V. (1986) Monoclonal Antibodies to Cyclosporin. Prog. Allergy, 38, 108.

7. Bayley, H. (1983) In: T. S. Work and R. H. Burdon (Eds.) Laboratory Techniques in Biochemistry and Molecular Biology, Photogenerated Reagents in Biochemistry and Molecular Biology. Elsevier, Amsterdam p. 15.

8. Wenger, R. M. (1986) Progress in the Chemistry of Organic Natural Products, 50, 123.

9. Erlanger, A. (1980) The Preparation of Antigenic Hapten-Carrier Conjugates: A Survey. Methods in Enzymology, 70, 85.

10. Hestrin, S. (1949) The reaction of acetylcholine and other carboxylic acid derivatives with hydroxylamine and its analytical application. J. Biol. Chem. 180, 249.

11. Cohen, W. and Erlanger, B. F. (1961) The presence of a second conformation —sensitive functional group at the active center of chymotrypsin. Biochem. Biophys. Acta 52, 604.

12. Sandoz Ltd. (1986) Insert of "Ciclosporin RIA-Kit," Fifth Edition, Basle, Switzerland.

13. Galardy, R. E., Craig, L. C. and Printz, M. P. (1973) Benzophenone triplet: A new photochemical probe of biological ligand-receptor interactions. Nature (London) New Biol. 242, 127.

14. Wenger, R. M. (1986) Cyclosporin and analogues: structural requirements of immunosuppressive activity. Transplant. Proc. 18, Suppl 5, 213.

15. Traber, T., Kuh, M., Rueegger, A., Lichti, H., Loosli, H. R., von Wartburg, A. (1977) Helvetia Chimica Acta, 59, 1480.

16. Wenger, R. (1983) Transplant Proc., Suppl 1, 2280.

17. Petcher, T. J., Weber, H. P., Rueegger, A. (1976) Helvetia Chimica Acta, 59, 1480.

18. Kahan, B. D. (1984) Am. J. Diseaes, 3, 444.

19. Chowdhry, V., Vaughan, R., Westheimer, F. H. (1976) Proc. Natl. Acad. Sci. USA, 73, 1406.

20. Gupta, C. M., Radhakrishnan, R., Gerber, G. E., Osen, W. L., Quay, S. C., Khorana, H. G. (1979) Proc. Natl. Acad. Sci. USA, 76, 2595.

21. Pascual, A., Casanova, J., Samuels, H. H. (1982) J. Biol. Chem., 257, 9640.

22. Guesdon, J. L., Ternynck, T., Avrameas, S. (1979) J. Histochem. Cytochem., 27, 1131.

23. Cleveland, WL. L, Wood, I., Cone, R. E., Iverson, G. M., Rosenstein, R. W., Gershon, R. K., Erlanger, B. F. (1981) Proc. Natl. Acad. Sci. USA, 78, 7697.

24. Habee, A. F. S. (1966) Anal. Biochem., 14, 328.

25. Bethell, G. S., Ayers, J. S., Hancock, W. S., Hearn, M. T. W. (1979) J. Biol. Chem., 254, 2572.

What is claimed is:

1. A compound having the structure:

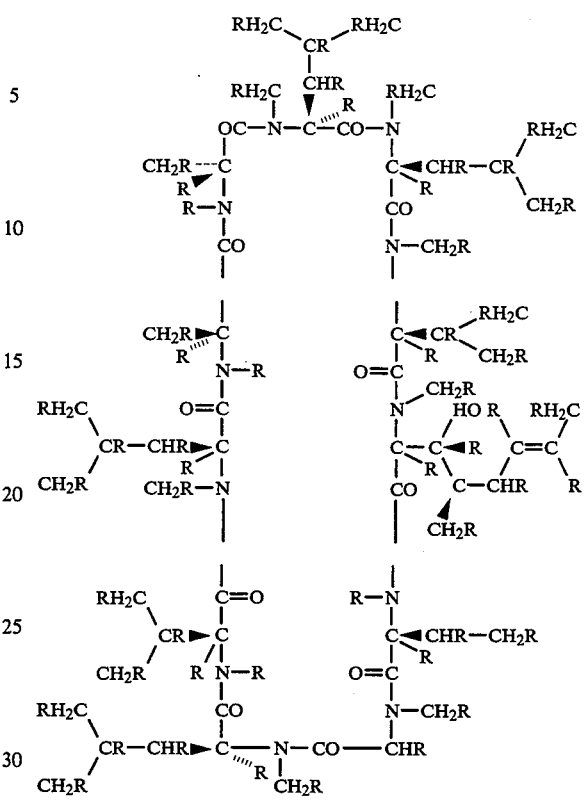

wherein a plurality of R's are X and the remainder are H, wherein X is a ligand comprising a reactive group and wherein X is bonded to the compound by a photochemical reaction between a hydrogen of cyclosporine A and a photochemically activatable precursor of X.

2. A composition of matter which comprises the compound of claim 1 and a polypeptide coupled to the compound through the reactive group on X.

3. The composition of matter of claim 2 wherein the polypeptide is a protein.

4. The composition of matter of claim 3 wherein the protein is bovine serum albumin.

5. The composition of matter of claim 3 wherein the protein is rabbit serum albumin.

6. The composition of matter of claim 3 wherein the protein is keyhole limpet hemocyanin.

7. The composition of matter of claim 3 wherein the protein is ovalbumin.

8. A monoclonal antibody directed against the composition of matter of claim 3 and specific for cyclosporine A or a congener of cyclosporine A.

9. The monoclonal antibody of claim 8 labeled with a detectable marker.

10. A method of detecting the presence of cyclosporine A or congener of cyclosporine A in a biological tissue sample which comprises treating the biological tissue sample with a detectably labeled antibody of claim 9 under conditions permitting the antibody to bind to cyclosporine A or congener and form a complex therewith, removing labeled antibody which is not bound to cyclosporine A or congener, detecting the presence of labeled antibody bound to cyclosporine A or congener and thereby detecting the presence of cyclosporine A or congener in the biological tissue sample.

11. A method of claim 10 wherein the biological tissue sample is kidney.

12. A method of detecting the presence of cyclosporine A or congener of cyclosporine A in a biological tissue sample which comprises treating the biological tissue sample with the antibody of claim 8 under conditions permitting the antibody to bind to cyclosporine A or congener and form a complex therewith, removing antibody which is not bound to cyclosporine A or congener, treating the complex with a labeled antibody directed to the unlabeled antibody under conditions such that the labeled antibody binds to the unlabeled antibody of the complex, removing labeled antibody which is not bound to the complex, detecting tke presence of labeled antibody bound to the complex and thereby detecting the presence of cyclosporine A or congener in the biological tissue sample.

13. A method of claim 12 wherein the biological tissue sample is kidney.

14. A method of determining the concentration of cyclosporine A or congener or cyclosporine A in a biological fluid sample which comprises:
  (a) contacting a solid support with an excess of the composition of matter of claim 3 under conditions permitting the composition of matter to attach to the surface of the solid support;
  (b) contacting a predetermined volume of biological fluid sample with a predetermined amount of a labeled antibody directed to the composition of matter of claim 3 and specific for cyclosporine A or congener of cyclosporine A under conditions such that the cyclosporine A or congener in the sample binds to the labeled antibody and forms a complex therewith;
  (c) contacting the resulting complex to the solid support to the surfaces of which the compositions of matter is attached under conditions permitting the labeled antibody of the complex to bind to the composition of matter;
  (d) treating the solid support so that only the composition of matter and labeled antibody of the complex bound thereto remain;
  (e) quantitatively determining the amount of labeled antibody of the complex bound to the composition of matter; and
  (f) thereby determining the concentration of cyclosporine A or congener in the biological fluid sample.

15. A method of claim 14 wherein the composition of matter is attached to the surface of the solid support by noncovalent bonds.

16. A method of claim 14 wherein the composition of matter is attached to the surface of the solid support by covalent bonds.

17. A method of claim 14 wherein the biological fluid is blood.

18. A method of claim 14 wherein the biological fluid is urine.

19. A method of claim 14 wherein the biological fluid is feces.

20. A method of claim 14 wherein the biological fluid is extracts of tissue.

21. A method of determining the concentration of cyclosporine A or congener of cyclosporine A in a biological fluid sample which comprises:
  (a) contacting a solid support with an excess of the composition of matter of claim 3 under conditions permitting the composition of matter to attach to the surface of the solid support; (b) contacting a predetermined volume of biological fluid sample with a predetermined amount of an antibody directed to the composition of matter of claim 3 and specific for cyclosporine A or congener of cyclosporine A under conditions such that the cyclosporine A or congener in the sample binds to the antibody and forms a complex therewith;
  (c) contacting this complex with a predetermined amount of labeled antibody directed to the unlabeled antibody under conditions such that the labeled antibody binds to the unlabeled antibody complex of step (b) and forms a labeled complex therewith;
  (d) contacting the resulting labeled complex to the solid support to the surface of which the composition of matter is attached under conditions permitting the unlabeled antibody bound to the labeled antibody of the labeled complex to bind to the composition of matter;
  (e) treating the solid support so that only the composition of matter and labeled complex bound thereto remain;
  (f) quantitatively determining the amount of labeled antibody of the labeled complex bound to the unlabeled antibody which is in turn bound to the composition of matter; and
  (g) thereby determining the concentration of cyclosporine A or congener in the biological fluid sample.

22. A method of claim 21 wherein the composition of matter is attached to the surface of the solid support by noncovalent bonds.

23. A method of claim 21 wherein the composition of matter is attached to the surface of the solid support by covalent bonds.

24. A method of claim 21 wherein the biological fluid is blood.

25. A method of claim 21 wherein the biological fluid is urine.

26. A method of claim 21 wherein the biological fluid is feces.

27. A method of claim 21 wherein the biological fluid is extracts of tissue.

28. A method of determining the concentration of cyclosporine A or congener of cyclosporine A in biological fluid sample by radioimmunoassay which comprises:
  (a) radioactively labeling a predetermined amount of a substance comprising cyclosporine A, congener of cyclosporine A or the composition of matter of claim 3;
  (b) adding the predetermined amount of radiolabeled substance to the biological fluid sample;
  (c) contacting the mixture of (b) with a predetermined amount of an antibody directed to the composition of matter of claim 3 and specific for cyclosporine A or congener of cyclosporine A under conditions suitable to permit the antibody to bind to the cyclosporine A or congener in the biological fluid sample and the labeled substance;
  (d) removing any unbound radiolabeled substance;
  (e) quantitatively determining the amount of labeled substance bound to the antibody; and
  (f) thereby determining the concentration of cyclosporine A or congener in the biological fluid sample.

29. A method of claim 28 wherein the biological fluid is blood.

30. A method of claim 28 wherein the biological fluid is urine.

31. A method of claim 28 wherein the biological fluid is feces.

32. A method of claim 28 wherein the biological fluid is extracts of tissue.

33. A method of monitoring levels of cyclosporine A or congener of cyclosporine A in a subject which comprises:

(a) taking biological fluid samples from a subject at predetermined intervals; and (b) determining the amount of cyclosporine A or congener in each biological fluid sample according to claim 14.

34. A method of monitoring levels of cyclosporine A or congener of cyclosporine A in a subject which comprises:

(a) taking biological fluid samples from a subject at predetermined intervals; and (b) determining the amount of cyclosporine A or congener in each biological fluid sample according to claim 21.

35. A method of monitoring levels of cyclosporine A or congener of cyclosporine A in a subject which comprises:

(a) taking biological fluid samples from a subject at predetermined intervals; and (b) determining the amount of cyclosporine A or congener in each biological fluid sample according to claim 28.

* * * * *